United States Patent [19]

Murib

[11] Patent Number: 4,918,257

[45] Date of Patent: Apr. 17, 1990

[54] CATALYTIC CONVERSION OF METHANE TO HIGHER HYDROCARBONS

[75] Inventor: Jawad H. Murib, Cincinnati, Ohio

[73] Assignee: Quantum Chemical Corporation, New York, N.Y.

[21] Appl. No.: 219,417

[22] Filed: Jul. 15, 1988

[51] Int. Cl.$^4$ .............................................. C07C 2/00
[52] U.S. Cl. ................................. 585/500; 585/654; 585/657; 585/661
[58] Field of Search ............... 585/500, 654, 657, 700, 585/661, 659

[56] References Cited

U.S. PATENT DOCUMENTS 4,684,800  1/1987  Withers, Jr. et al. ............... 585/500

FOREIGN PATENT DOCUMENTS 3503664  8/1986  Fed. Rep. of Germany .
63-626    3/1988  Japan .
8607351  12/1986  PCT Int'l Appl. .

OTHER PUBLICATIONS

Keller et al., Journal of Catalysis, 73, 9–19 (1982).
Chemical Abstract 107:39121t of Imamura et al., Chem. Express 2, No. 1, 49–52 (1987).

Primary Examiner—Ferris H. Lander
Assistant Examiner—James M. Hunter, Jr.
Attorney, Agent, or Firm—Kenneth D. Tremain; Gerald A. Baracka

[57] ABSTRACT

A process for making ethylene, ethane and other higher hydrocarbons from methane is disclosed. In this process methane is contacted with oxygen in the presence of at least one metal of Group IB of the Periodic Table of the Elements, with the proviso that if the metal is copper an additional Group IB must be present, a metal-containing chloride or a metal-containing compound capable of being formed into a metal-containing chloride in situ, where the metal is manganese, an alkali metal, an alkaline earth metal or a rare earth metal of the lanthanide series, and a volatile halide.

28 Claims, No Drawings

CATALYTIC CONVERSION OF METHANE TO HIGHER HYDROCARBONS

BACKGROUND OF THE DISCLOSURE

1. Field of the Invention

The present invention is directed to a process for converting methane to higher hydrocarbons, especially ethylene. More specifically, the present invention is directed to a process for converting methane to higher hydrocarbons, especially ethylene, utilizing a catalytic system which includes a Group IB metal, a chloride of an alkali metal, an alkaline earth metal or a rare earth metal of the lanthanide series and a volatile halide.

2. Background of the Prior Art

New and improved processes for synthesizing higher hydrocarbons, that is, hydrocarbons containing at least two carbon atoms, especially ethylene, from methane have been a continuing aim of those skilled in the art. This is to be expected in that while methane is readily available at low cost, the higher hydrocarbon product of such processes, such as ethylene, is far more costly and useful. Ethylene and other higher hydrocarbons are valuably utilized as intermediates in the production of liquid fuels, plastics, fibers, solvents and a plurality of other organic compounds used in the chemical process industries.

Because of this obvious attractiveness of employing low cost and readily available methane in the synthesis of higher value higher hydrocarbons, a multiplicity of processes utilizing methane as a source of these higher hydrocarbons have been developed. Among the more relevant of these processes disclosed in the prior art are processes utilizing metal oxide catalysts. One such teaching is G.E. Keller et al., *Journal of Catalysis*, Vol. 73, 9-19 (1982). Keller et al. describes a method for synthesizing ethylene by the oxidative coupling of methane In this method methane is converted, in a gas phase catalytic reaction, to ethylene and ethane at atmospheric pressure and a temperature of from 500° C. to 1000° C. The catalyst used in this reaction is selected from the group consisting of an oxide of tin, lead, bismuth, antimony, tellurium, cadmium and manganese supported on alumina. Of particular interest is the conclusion that many metal oxides, including silver and copper, show little or no activity as catalysts in this reaction.

A more recent disclosure, S. Imamura et al. *Chem Express*, Vol. 2 (1), 49-52 (1987), discloses that silver oxide in admixture with lead oxide catalyzes the oxidative dimerization of methane to ethylene and ethane.

Yet a third reference directed to the use of oxides of Group IB metals as catalysts in the conversion of methane is the PCT application, WO 86/07351. That patent application discloses a process and catalyst for the synthesis of hydrogen, ethylene, ethane and higher hydrocarbons from methane in the presence of oxygen. The catalyst utilized in this process is an oxide of a metal selected from the group consisting of a Group IIA metal, a Group IIIA metal, a lanthanide series metal excluding cerium and mixtures thereof. Optionally, a promoter for the catalyst, an oxide of a metal selected from a Group IA metal, a Group IIA metal, a Group IIIA metal, a lanthanide series metal, a Group IVB metal, a Group VB metal, a Group IB metal or mixtures thereof may also be utilized.

In addition, Group IB metals in other than the oxide state have been suggested for use in the synthesis of ethylene and other hydrocarbons from methane. One such teaching is included in German Pat. Publication 3,503,664. The '664 patent publication claims the use of silver halides, among other materials, as catalysts in the catalytic oxidation of methane with oxygen at elevated temperatures, i.e. 600° C., to 1,000° C., to yield ethylene and ethane while co-feeding hydrogen chloride therewith.

It is emphasized that an discussion of processes employing Group IB metals as catalysts in the conversion of methane to higher hydrocarbons must include the disclosure in U.S. Pat. 4,684,800. The '800 patent teaches a method for converting methane to higher hydrocarbons by contacting methane, an oxygen-containing gas and a reducible metal oxide in the presence of at least one promoter selected from the group consisting of halogens and halogen compounds. The preferred metals of the reducible metal oxide comprise manganese, tin, indium, germanium, antimony, lead, bismuth and mixtures thereof. In addition, cerium, praseodymium or terbium rare earth metal oxide can be utilized as can reducible iron or ruthenium oxides when associated with an alkali metal component and/or an alkaline earth metal component.

Of particular interest is the disclosure in the '800 patent requiring that the reaction occur in the substantial absence of a catalytically effective amount of nickel, noble metals or compounds thereof. Specifically, the '800 patent states that the presence of Group IB metals silver and gold as well as nickel, rhodium, palladium, osmium, iridium and platinum have a deleterious catalytic effect on this reaction. The disclosure states that these metals when contacted with methane at reaction temperature i.e., 800° C. to 900° C., tend to promote coke formation as well as combustion products rather than the desired products, ethylene and higher hydrocarbons.

In summary, the prior art description relating to the use of a Group IB metal as a catalyst in the catalytic transformation of methane to higher hydrocarbons, especially ethylene, is none too promising. The weight of the teaching of the references suggest that these metals do not present a fruitful avenue for future research to bring to fruition this desirable transformation. However, the earlier remarks establishing the strong desirability of providing new processes to effectuate this reaction urge workers in this art to examine and reevaluate all possible catalytic agents that may effectuate the reaction of methane to produce ethylene.

SUMMARY OF THE INVENTION

It has now been discovered that a process for converting methane to higher hydrocarbons, especially ethylene, can be accomplished in an oxidation reaction involving a reaction with oxygen or an oxygen-containing gas. This catalytic reaction provides commercially acceptable yields Although the catalyst involves Group IB metals, the catalyst system is completely novel. Nothing in the prior art so much as suggested that the unexpected results noted could be obtained by this system.

In accordance with the present invention a process for making higher hydrocarbons from methane is disclosed. In this process methane is contacted with oxygen in the presence of at least one metal of Group IB of the Periodic Table of the Elements, with the proviso that if the metal is copper an additional Group IB metal must be present, a metal-containing chloride or a metal-containing compound capable of being formed into a metal-containing chloride in situ, where the metal is an alkali metal, an alkaline earth metal, manganese or a rare earth metal of the lanthanide series, and a volatile halide.

DETAILED DESCRIPTION

The present invention is directed to a process for making higher hydrocarbons, especially ethylene, by the catalytic reaction of methane and oxygen. Although the primary higher hydrocarbon produced in the process of the present invention is ethylene, a significant amount of ethane is produced along with smaller amounts of unsaturated $C_3$ and $C_4$ hydrocarbons.

This process employs a unique catalyst system. The catalyst system includes a Group IB metal, but is limited to the metal. It is important to emphasize that the Group IB metals must be provided in the metallic state, i.e., the metal in the zero valent state. At least one of the Group IB metals, copper, gold and silver, must be present although two or all three of the metals may be utilized. The sole additional requirement is that if copper is employed at least one additional Group IB metal, gold or silver, must also be part of the catalyst system. Copper may be initially present in conjunction with silver and/or gold, however, under the reaction conditions, it may volatilize from the reaction zone leaving a more active catalyst than that obtained starting with silver and/or gold alone.

The Group IB metal present in the catalyst system of the present invention, consistent with the proviso requiring that copper be present with at least one other Group IB metal, is selected from the group consisting of silver, gold, a mixture of silver and gold, a mixture of silver and copper, a mixture of gold and copper, a mixture of silver, gold and copper, an alloy of silver and gold, an alloy of silver and copper, an alloy of gold and copper, an alloy of silver, gold and copper and mixtures thereof. More preferably, the Group IB metal is silver, a mixture of silver and copper or an alloy of silver and copper. Most preferably, the Group IB metal, utilized in the process of the present invention, is silver.

A second essential component of the catalyst system used in the process of the present invention is a metal-containing chloride compound or a compound capable of being formed into a metal-containing chloride in situ. Specifically, the second component of the catalyst system is a preformed chloride of an alkali metal, a chloride of an alkaline earth metal, a manganese chloride or a chloride of a rare earth metal of the lanthanide series or one of the above-enumerated chlorides so formed under reaction conditions in situ. Of these metal-containing chlorides or metal-containing compounds capable of being formed into metal-containing chlorides in situ, alkali metal chlorides and alkaline earth metal chlorides or compounds of being transformed thereto in situ are preferred. Of these compounds, sodium chloride and strontium chloride are particularly preferred.

The third and last essential component of the catalyst system utilized in the process of the present invention is a volatile halide. The preferred volatile halides useful in the catalyst system of the instant invention include hydrogen halides, halogen gases, halide substituted methanes and mixtures thereof. The halide substituted methanes include carbon tetrahalides, trihalide-substituted methane, dihalo-substituted methane and halomethanes. That is, the hydrogen atoms in methane may be substituted with not only one halogen but with atoms of two or more different halogens. It is furthermore noted that mixtures two or more of the above-discussed volatile halides may be employed.

Examples of volatile halides within the contemplation of this invention include, but are not limited to, chlorine gas, bromine gas, hydrogen chloride, hydrogen bromide, carbon tetrachloride, carbon tetrabromide, chloroform, dichloromethane, methyl chloride, methyl bromide, dibromomethane, fluorochloromethane, mixtures thereof and the like.

Of the volatile halides, hydrogen halides, halogens, carbon tetrahalides, haloforms, di-halomethanes and mono-halomethanes and mixtures thereof are preferred. More preferably, the volatile halide is selected from the group consisting of hydrogen halides, halogens, carbon tetrahalides and monohalomethanes. Still more preferably, the volatile halide is a hydrogen halide, a carbon tetrahalide or a monohalomethane. Even more preferred, the volatile halide is hydrogen chloride, methyl chloride or carbon tetrachloride. Most preferably, the volatile halide is hydrogen chloride or methyl chloride.

The thermodynamic conditions under which the process of the present invention occurs involves a reaction occurring at a temperature in the range of between about 650° C. and about 1,000° C. More preferably, the temperature of reaction is in the range of between about 700° C. and about 900° C. Still more preferably, the reaction occurs at a temperature of from about 725° C. to about 850° C. Most preferably, the reaction occurs at a temperature between about 735° C. and about 825° C.

The reaction occurs at a pressure in the range of between atmospheric pressure and 1,000 pounds per square inch (psi). Preferably, the process of the present invention occurs at a pressure in the range of between atmospheric pressure and 700 psi. More preferably, the pressure of the process of this invention is between atmospheric and about 500 psi. Most preferably, the pressure of the reaction is atmospheric up to about 250 psi.

The catalytic system, in a preferred embodiment, is supported. That is, the Group IB metal and the metal-containing chloride or a metal-containing compound capable of being formed into a metal-containing chloride in situ are disposed on carrier. Among the carriers that can be used as a support for the catalyst system of the present invention are silica, alumina, silicon carbide, titania, zirconia and naturally occurring materials which incorporate one or more of these materials. For example, pumice, a naturally occurring material which comprises silica and alumina, can be effectively employed as a carrier for the catalytic constituents of the present invention. It is emphasized, of course, that the volatile halide constituent is provided as a gaseous stream and is not disposed upon the carrier in those applications where the catalyst is supported.

The following examples are given to illustrate the scope of the present invention. Because these examples are given for illustrative purposes only, the scope of the invention should not be limited thereto.

EXAMPLE 1

A mixture of 3.9 g. silver nitrate and 1.9 g. copper nitrate hydrate having the formula $Cu(NO_3)_2.3H_2O$ was dissolved in a sufficient amount of water to wet 50 g. of pumice (bulk volume,110 ml). The impregnated pumice was dried, calcined in air at 450° C. for 3 hours, treated with hydrogen at 450° C. for 3 hours and cooled under nitrogen to yield a mixture of supported metallic copper and silver A 5 ml. sample (bulk volume) of the supported silver and copper was impregnated with an aqueous solution of 0.3 g. sodium chloride dissolved in 2.5 ml. of deionized water. The water was evaporated by tumbling the catalyst in a rotating dish while being subjected to hot air supplied by a heat gun. The dried catalyst was packed into the lower half of a quartz tube (12 mm. ID by 50 cm.) provided with a thermocouple encased in a thermowell imbedded in the catalyst bed. The tube was mounted vertically inside two 15 cm. high electric furnaces so that the upper furnace, maintained at 400° C., acted as a preheater and the lower furnace, operated at 750° C., provided heat to the reactor. The reactor operated at 750° C. was maintained under an atmosphere of nitrogen until the reactants were charged therein.

Upon reaching a steady state condition of 750° C. at atmospheric pressure, the nitrogen stream was replaced with a reaction feed which comprised a stream of 32 mole percent methane, 8 mole percent oxygen, 58 mole percent nitrogen and 2 mole percent methyl chloride. The feed rate was sufficient to provide a 0.5 second contact time based on the catalyst bulk volume. Alternatively, contact time may be expressed as gas hourly space velocity. The units of gas hourly space velocity are liters of gas per liter of catalyst per hour, or reciprocal hours. Thus, those skilled in the art are aware that the 0.5 second contact time of this example is equivalent to 7,200 reciprocal hours.

The effluent product of this catalyzed reaction was analyzed by gas chromatography and mass spectrometry. This analysis established that 24% of the methane was converted with a carbon selectivity of 71% to higher hydrocarbons (distribution: 83 percent ethylene, 9 percent ethane and 8 percent unsaturated $C_3$ and $C_4$ hydrocarbons).

The results of this example are summarized in Table 1.

EXAMPLE 2

Example 1 was duplicated but for a reduction in contact time from 0.5 second to 0.4 second. The result of this experiment, as determined by gas chromatography and mass spectrometry analyses, was that 20% of the methane was converted with a carbon selectivity of 80 mole percent to higher hydrocarbons (distribution: 65 percent ethylene; 28 percent ethane; and 7 percent unsaturated $C_3$ and $C_4$ hydrocarbons). Thus, operating under a shorter contact time led to higher selectivity with lower conversion.

EXAMPLE 3

Example 1 was duplicated but for a further reduction in contact time from 0.5 second to 0.2 second. Analysis of the reactor effluent showed that 14% of the methane was converted with a carbon selectivity of 84 mole % to higher hydrocarbons. Again, operation under a shorter contact time led to higher selectivity with lower conversion.

COMPARATIVE EXAMPLE 1

Example 1 was repeated except that methyl chloride was omitted from the feed. Analysis of the reactor effluent showed that 3% of the methane was converted with a carbon selectivity of 61 mole % to higher hydrocarbons. This result showed that, in the absence of methyl chloride, the catalyst system exhibited low conversation even in the presence of sodium chloride.

COMPARATIVE EXAMPLE 2

Example 1 was repeated except that sodium chloride was omitted from the catalyst. Analysis of the reactor effluent showed that 8% of the methane was converted with a carbon selectivity of 31 mole % to higher hydrocarbons. Combustion was the dominant reaction in that 69% of the converted methane yielded carbon oxides. This result showed that, in the absence of sodium chloride, the selectivity to higher hydrocarbon was poor despite the presence of a volatile halide, e.g., methyl chloride, in the feed.

The results of Example 1 and Comparative Examples 1 and 2 illustrate that the presence of sodium chloride in the catalyst system and of methyl chloride in the gaseous feed are required for commercially significant methane conversion to higher hydrocarbons.

The results of Comparative Example 2 are summarized in Table 1.

EXAMPLE 4

Example 1 was repeated but for a substitution of the metal-containing chloride compound. In Example 1 the metal-containing chloride compound was sodium chloride. In this example, sodium chloride was replaced with another alkali metal chloride, lithium chloride. Parallel to Example 1, the copper and silver catalyst supported on pumice was impregnated with an aqueous solution of lithium chloride, instead of the sodium chloride. In addition, whereas in Example 1 0.3 g. of sodium chloride was dissolved in 2.5 ml. of deionized water prior to impregnation onto the supported catalyst, in this example 0.2 g. of lithium chloride dissolved in 2.5 ml. of deionized water was used.

The process of Example 1 was thereafter duplicated. Analysis of the results of this example, accomplished again by gas chromotography and mass spectrometry of the product effluent, established that 26% of the methane was converted with a carbon selectivity of 58 mole % to higher hydrocarbons (distribution: 80 percent ethylene and 20 percent ethane).

EXAMPLE 5

Example 4 was repeated except for a decrease in contact time from 0.50 second to 0.25 second. The result of this change was evidenced in the effluent analysis which showed that 18% of the methane was converted with a carbon selectivity of 76 mole % to higher hydrocarbons (distribution of 61 percent ethylene and 39 percent ethane). Again, operating under a shorter contact time led to higher selectivity at lower conversion.

EXAMPLE 6

Example 1 was repeated except that samarium chloride ($SmCl_3 \cdot 6H_2O$, 1.83 g) was used instead of sodium chloride. The reactor feed was 66.9 mole % $CH_4$, 6.4 mole % $O_2$, 25.5 mole % $N_2$ and 1.2 mole % $CH_3Cl$.

Analysis of the reactor effluent indicated that 5% of the methane was converted with a carbon selectivity of 65 mole % to higher hydrocarbons (distribution: 69% ethylene and 31% ethane).

EXAMPLE 7

A catalyst containing 2 wt % Cu, 6.2 wt % $K_2CO_3$ and 4.2 wt % NaOH supported on pumice was prepared by impregnating the pumice support with appropriate amounts of cupric nitrate and potassium carbonate. The impregnated solid was dried for 1 hour at 110° C., followed by heating in nitrogen at 450° C. for 3 hours and then treated with hydrogen at 450° C. for 3 hours. A sample of this solid was finally impregnated with an appropriate amount of sodium hydroxide and dried at 110° C. for one hour.

This solid catalyst was tested using the procedure of Example 1 except that the gaseous feed comprised: 59 mole methane, 9 mole % oxygen, 30 mole % nitrogen and 2 mole % methyl chloride. It is known that under the reaction conditions, methyl chloride in the feed undergoes pyrolysis to generate hydrogen chloride (U.S. Pat. 4,714,769) which reacts with potassium carbonate and sodium hydroxide to form the corresponding chlorides in situ. Analysis of the reactor effluent showed that 10% of the methane was converted with carbon selectivity of 69 mole % to higher hydrocarbons (distribution: 74% ethylene and 25% ethane with the balance being higher hydrocarbons).

EXAMPLE 8

Example 1 was repeated except that the catalyst did not include copper. That is, the pumice supported catalyst included silver but not copper. Otherwise, Example 1 was reproduced in its entirety in this example.

An analysis of the reactor effluent showed that 21% of the methane was converted with a carbon selectivity of 65 mole % to higher hydrocarbons (distribution: 82% ethylene, 11% ethane and 7% unsaturated $C_3$ and $C_4$ hydrocarbons).

The results of this example are tabulated in Table 1.

TABLE 1

| Example No. | Catalyst on Pumice | % $CH_4$ Conversion | % Carbon Selectivity | | | | Total Hydrocarbons |
|---|---|---|---|---|---|---|---|
| | | | $C_2H_4$ | $C_2H_6$ | $C_{3+}$ | $CO_x$ | |
| 1 | Ag—Cu—NaCl | 27 | 60 | 5 | 6 | 29 | 71 |
| 8 | Ag—NaCl | 21 | 53 | 7 | 5 | 35 | 65 |
| CE2 | Ag—Cu | 8 | 23 | 8 | trace | 69 | 31 |

DISCUSSION OF TABLE 1

The results of Examples 1, 8 and CE2 establish the criticality of the presence of a metal-containing chloride or a metal-containing compound capable of being converted to a metal-containing chloride in-situ in the ethylene forming reaction. The absence of sodium chloride in Comparative Example 2, compared to its presence in Examples 1 and 8, results in far lower values of both methane conversion and selectivity to higher hydrocarbons.

EXAMPLE 9

Example 8 was repeated except that manganous chloride ($MnCl_2 \cdot 4H_2O$, 1.0 g.) was used instead of sodium chloride and the reaction feed was identical with that of Example 6. That is, the catalyst comprised metallic silver and manganous chloride supported on pumice. The gaseous feed, 66.9 mole % $CH_4$, 6.4 mole % $O_2$, 25.5 mole % $N_2$ and 1.2 mole % $CH_3Cl$, was fed into the reactor.

Analysis of the reactor effluent indicated a 13% methane conversion with carbon selectivity of 70 mole % to higher hydrocarbons.

The results of this example, including distribution, are included in Table 2.

COMPARATIVE EXAMPLE 3

Example 9 was duplicated but for the absence of metallic silver on the pumice support. The methane-containing gaseous feed thus reacted resulted in an 11% conversion of methane with 49 mole % carbon selectivity to higher hydrocarbons.

The full results of this example appear in Table 2.

TABLE 2

| Example No. | Catalyst on pumice | % $CH_4$ Conv. | Mole % Carbon Selectivity | | | | Total Hydrocarbons |
|---|---|---|---|---|---|---|---|
| | | | $C_2H_4$ | $C_2H_6$ | $C_{3+}$ | $CO_x$ | |
| 9 | Ag—$MnCl_2$ | 13 | 49 | 14 | 7 | 30 | 70 |
| CE 3 | $MnCl_2$ | 11 | 33 | 13 | 3 | 51 | 49 |

DISCUSSION OF TABLE 2

The results summarized in Table 2 establish the advantage of a Group IB metal, in this case silver, in the selective conversion of methane to ethylene and other higher hydrocarbons.

EXAMPLE 10

A 5.4 g. sample (bulk volume 5 ml) of a commercially available supported silver catalyst (8 wt. % Ag on alumina, manufactured by Harshaw) was impregnated with sodium chloride to obtain a loading of 2 weight % NaCl and tested under the conditions of Example 1, except that the feed was altered. The gaseous feed of Example 10 comprised 92.8 mole % methane, 7 mole % oxygen and 0.25 mole % carbon tetrachloride.

Analysis of the reactor effluent indicated a 6% methane conversion with 79 mole % carbon selectivity to higher hydrocarbons.

The results of Example 10 are included in tabular summary in Table 3.

COMPARATIVE EXAMPLE 4

Example 10 was repeated except that sodium chloride was omitted from the alumina-supported catalyst and carbon tetrachloride was not included in the gaseous feed.

Analysis of the reactor effluent showed that 7% of the methane was converted with a carbon selectivity to higher hydrocarbons of 20 mole % and to carbon oxides (combustion) of 80 mole %.

A summary of Comparative Example 4 appears in Table 3.

COMPARATIVE EXAMPLE 5

This example reproduced Example 10 except that alumina-supported silver chloride (8% as Ag) was used instead of elemental silver. The catalyst was prepared by impregnating an alumina support with an appropriate amount of aqueous silver nitrate solution. The dried solid was treated with an equivalent amount of aqueous 10 wt % HCl solution and washed until free of soluble chloride ions. The washed solid was then dried in air at 110° C. The resulting alumina supported silver chloride was impregnated with sodium chloride and reacted with the feed, and in accordance with the procedure, of Example 10.

Analysis of the reactor effluent indicated a 6% methane conversion with a carbon selectivity of 15 mole % to higher hydrocarbons, the balance representing combustion products of carbon.

A summary of Comparative Example 5 is included in Table 3.

COMPARATIVE EXAMPLE 6

Comparative Example 5 was repeated with the same catalyst of silver chloride on alumina except that NaCl was not impregnated onto the alumina-supported silver chloride nor was $CCl_4$ included in the gaseous feed of Example 10.

Analysis of the reactor effluent established a 5% methane conversion with a carbon selectivity of 9 mole % to higher hydrocarbons, the balance being combustion.

Comparative Example 6 is provided in tabular form in Table 3, along with the results of Examples 10, CE4 and CE5.

Example 4 but for the substitution of silver chloride for silver in the catalyst system.

Even in the presence of sodium chloride and a volatile halide within the scope of the present invention, as exemplified in Comparative Example 5, the catalyst system utilizing silver chloride provides an unacceptably low selectivity to ethylene and higher hydrocarbons. More significantly, a comparison of Comparative Example 5 and Example 10 dramatically demonstrates the unexpectedly improved result obtained by the use of silver instead of silver chloride. The experiments of Example 10 and Comparative Example 5 were identical but for the use of silver in Example 10 and silver chloride in Comparative Example 5. The remarkable difference in selectivity between Example 10 (79% to ethylene and other higher hydrocarbons) and Comparative Example 5 (15% to ethylene and other higher hydrocarbons) for the same 6% of methane converted establishes the advance in the art of the present invention.

EXAMPLE 11

Example 1 was repeated except that the catalyst comprised metallic silver and strontium oxide prepared by simultaneous deposition of the corresponding nitrates on pumice. Thus, a dry sample of pumice weighing 34.4 g. (75 ml bulk volume), which was pre-washed with water, was mixed with a 30 ml aqueous solution containing 12.74 g. $AgNO_3$ and 15.87 g. $Sr(NO_3)_2$. The mixture was tumbled on a rotating dish and dried with hot air provided by a heat gun. The mixture was then stored overnight in an air heated oven at 120° C. The resulting solid was packed in an alumina tube provided with a thermocouple encased in a thermowell placed in the middle of the bed and the solid was heated to 500°

TABLE 3

| Example No. | Catalyst System | | | % Conv. | % Carbon Selectivity | |
|---|---|---|---|---|---|---|
| | Gp IB Component | MCl, wt % | Vol. Halide, mol % | $CH_4$ | $C_2H_4$ & Higher Hyd. | $CO_2$ & CO |
| 10 | Ag | NaCl, 2 | $CCl_4$, 0.25 | 6 | 79 | 21 |
| CE4 | Ag | None | None | 7 | 20 | 80 |
| CE5 | AgCl | NaCl, 2 | $CCl_4$, 0.25 | 6 | 15 | 85 |
| CE6 | AgCl | None | None | 5 | 9 | 91 |

DISCUSSION OF TABLE 3

The results summarized in Table 3 establish several important conclusions. First, Comparative Example 4 establishes that the presence of a silver catalyst alone is insufficient to catalyze the reaction of methane and oxygen to produce ethylene and higher hydrocarbons. In Example 10, two weight percent sodium chloride and 0.25 mole percent carbon tetrachloride was incorporated in the supported catalyst and the feed, respectively. Otherwise, the two examples were identical. It is noted that whereas the conversion of methane was substantially the same in Example 10 and Comparative Example 4, the selectivity to ethylene and higher hydrocarbons was four times greater utilizing the catalyst system of the present invention, exemplified in Example 10, compared to a catalyst system employing only silver, illustrated by Comparative Example 4.

A second critical conclusion of these examples is the necessity of using elemental silver rather than a silver halide catalyst. Indeed, even in the absence of sodium chloride and a volatile halide, elemental silver, as exemplified in Comparative Example 4, produced better results, albeit, unacceptably low, than does Comparative Example 6 which was identical to Comparative C. using a programmed temperature rise of 10° C./min. under a nitrogen atmosphere. This was followed by heating in air at 500° C. for 2.5 hrs. After purging with nitrogen for 30 minutes, the solid was treated with a mixture of hydrogen and nitrogen (5 mole % $H_2$) at 500° C. for 2.5 hrs. and finally cooled to room temperature under a nitrogen atmosphere.

A 5 ml. sample of the thus formed catalyst was tested under the conditions of methane oxidation as carried out in Example 1 except that the gaseous feed of that example, which included 2 mole % methyl chloride, was replaced with 2 mole % hydrogen chloride. Analysis of the reactor effluent showed that 12% of the methane was converted with 60 mole % selectivity to higher hydrocarbons (distribution: 78% ethylene, 18% ethane, and 4% $C_{3+}$ higher hydrocarbons).

It is noted that this example demonstrates the use of a metal-containing compound capable of forming a metal-containing chloride in situ. That is, the metal-containing compound, strontium oxide, is converted in situ to strontium chloride by reaction of the oxide with the hydrogen chloride component of the gaseous feed. The presence of strontium chloride in the spent catalyst was confirmed by X-ray analysis.

COMPARATIVE EXAMPLE 7

Example 11 was repeated except that the catalyst did not include silver. That is, silver nitrate was not deposited on pumice followed by oxidation in air and hydrogenation by treatment with hydrogen, both at 450° C. The catalyst thus comprised strontium oxide supported on pumice.

Analysis of the reactor effluent indicated a methane conversion of 16% with a carbon selectivity of 43 mole % to higher hydrocarbons.

A comparison with the results of Example 11 show that the presence of silver and strontium oxide yields a 39% improvement in selectivity to higher hydrocarbons over that obtained with strontium oxide alone.

EXAMPLE 12

Example 8 was repeated except that 10.7 wt % silver was supported on silicon carbide, instead of pumice, and strontium chloride ($SrCl_2.6H_2O$, 1.38 g.), instead of sodium chloride, was employed. In addition, the reactor feed contained hydrogen chloride instead of methyl chloride.

Analysis of the reactor effluent showed that 19% of the methane was converted with a carbon selectivity of 61 mole % to higher hydrocarbon (distribution: 91% ethylene, 7% ethane, 2% $C_3+$) with 2% to methyl chloride.

COMPARATIVE EXAMPLE 8

Example 11 was repeated except that sodium oxide and silver oxide were used instead of strontium oxide and silver, respectively. Both oxides were formed by calcining the corresponding nitrates and omitting the hydrogenation step. The latter omission avoided the reduction of the silver oxide to metallic silver. That is, the catalyst comprised mixed silver oxide and sodium oxide which, upon reaction with hydrogen chloride in the feed, formed sodium chloride in situ.

Analysis of the reactor effluent indicated that 7% of the methane was converted. The products of carbon combustion were the major reaction products. The carbon selectivity was 42 mole % to higher hydrocarbons and 58 mole % to carbon oxides.

This example demonstrates that silver oxide is not selective even in the presence of sodium chloride.

The above embodiments and examples are given to illustrate the scope and spirit of the present invention. These embodiments and examples will make apparent, to those skilled in the art, other embodiments and examples. These other embodiments and examples are within the contemplation of the instant invention. Therefore, the invention should be limited only by the appended claims.

What is claimed is:

1. A process for making higher hydrocarbons from methane comprising contacting methane with oxygen or an oxygen-containing gas in the presence of: a catalyst comprising
   (a) at least one metal in the elemental state of Group IB of the Periodic Table of the Elements, with the proviso that if the metal is copper an additional Group IB metal must also be present;
   (b) a metal-containing chloride or a metal-containing compound formed in-situ into a metal-containing chloride, said metal of said metal-containing chloride or said metal-containing compound formed in-situ into a metal-containing chloride selected from the group consisting of manganese, an alkali metal, an alkaline earth metal and a rear earth metal of the lanthanide series; and
   (c) a volatile halide.

2. A process in accordance with claim 1 wherein said metal of Group IB is selected from the group consisting of silver, gold, a mixture of silver and gold, a mixture of silver and copper, a mixture of gold and copper, a mixture of silver, gold and copper, an alloy of silver an gold, an alloy of silver and copper, an alloy of gold and copper, an alloy of silver, gold and copper and mixtures thereof.

3. A process in accordance with claim 2 wherein said Group IB metal is selected from the group consisting of silver, a mixture of silver and copper and an alloy of silver and copper.

4. A process in accordance with claim 3 wherein said Group IB metal is silver.

5. A process in accordance with claim 1 wherein said metal of said metal-containing chloride whether directly provided or formed from a metal-containing compound in situ is an alkali metal or an alkaline earth metal.

6. A process in accordance with claim 5 wherein said metal-containing chloride is selected from the group consisting of sodium chloride and strontium chloride.

7. A process in accordance with claim 6 wherein said metal-containing chloride is strontium chloride.

8. A process in accordance with claim 6 wherein said metal-containing chloride is sodium chloride.

9. A process in accordance with claim 1 wherein said volatile halide is selected from the group consisting of hydrogen halides, halogen gases, halide-substituted methanes and mixtures thereof.

10. A process in accordance with claim 9 wherein said volatile halide is selected from the group consisting of hydrogen halides and halide-substituted methanes.

11. A process in accordance with claim 10 wherein said volatile halide is carbon tetrachloride.

12. A process in accordance with claim 10 wherein said volatile halide is hydrogen chloride.

13. A process in accordance with claim 10 wherein said volatile halide is methyl chloride.

14. A process in accordance with claim 1 wherein said process is conducted at a temperature in the range of between about 650° C. and about 1,000° C. and at a pressure in the range of between atmospheric and about 1,000 psi.

15. A process in accordance with claim 14 wherein said process occurs at a temperature of between about 700° C. and about 900° C. and at a pressure of between atmospheric and about 700 psi.

16. A process in accordance with claim 15 wherein said process occurs at a temperature of about 725° C. to about 850° C. and at a pressure of atmospheric to about 500 psi.

17. A process in accordance with claim 16 wherein said process occurs at a temperature in the range of between about 735° C. and about 825° C. and at a pressure in the range of between atmospheric and about 250 psi.

18. A process in accordance with claim. 1 wherein said Group IB metal and said metal-containing chloride or said metal-containing compound formed into a metal-containing chloride in situ are deposited upon a carrier.

19. A process in accordance with claim 18 wherein said carrier is selected from the group consisting of silica, alumina, silicon carbide, titania, zirconia and naturally occurring materials which incorporate one or more of any of the above materials.

20. A process for making higher hydrocarbons from methane comprising contacting methane with oxygen or an oxygen-containing gas at a temperature in the range of between about 650° C. and about 1,000° C. and a pressure in the range of between about atmospheric and about 1,000 psi in the presence of a catalyst comprising:
  (a) at least one metal in the elemental in the elemental state of Group IB of the Periodic Table of the Elements, with the proviso that if the metal is copper an additional Group IB metal must also be present;
  (b) a metal-containing chloride or a metal-containing compound formed in-situ into a metal-containing chloride, said metal of said metal-containing chloride or said metal-containing compound formed in-situ into a metal-containing chloride selected from the group consisting of manganese, an alkali metal and an alkaline earth metal; and
  (c) a volatile halide selected from the group consisting of hydrogen halides and halide substituted methanes.

21. A process in accordance with claim 20 wherein said Group IB metal is silver, said metal-containing chloride whether directly provided or formed in-situ from a metal-containing compound is selected from the group consisting of sodium chloride and strontium chloride and said volatile halide is selected from the group consisting of hydrogen chloride, methyl chloride and carbon tetrachloride, said process occurring at a temperature in the range of between about 700° C. and about 850° C. and a pressure in the range of between atmospheric and about 700 psi.

22. A process in accordance with claim 21 wherein said metal-containing chloride is sodium chloride and said volatile halide is methyl chloride, said process occurring at a temperature in the range of between about 725° C. and 850° C. and at a pressure of between atmospheric and about 500 psi.

23. A process in accordance with claim 20 wherein said Group IB metal and said metal-containing chloride or metal-containing compound formed into a metal-containing chloride in situ is disposed on a carrier.

24. A process in accordance with claim 23 wherein said carrier is selected from the group consisting of silica, alumina, silicon carbide, titania, zirconia and naturally occurring materials which incorporate one or more of the above inert materials.

25. A process in accordance with claim 24 wherein said carrier is selected from the group consisting of pumice, alumina and silicon carbide.

26. A process for making higher hydrocarbons from methane comprising contacting methane with a gaseous stream of oxygen or an oxygen-containing gas and a volatile halide in the presence of a catalyst formed by the steps comprising:
  (a) depositing silver nitrate and strontium nitrate on a carrier selected from the group consisting of alumina, silicon carbide and pumice; and
  (b) hydrogenating said deposited silver nitrate and strontium nitrate.

27. A process in accordance with claim 26 wherein said volatile halide is present in a concentration of between about 0.25 mole % and about 1.2 mole %, said concentration based on the total molar concentration of said gaseous reactants and said volatile halide.

28. A process in accordance with claim 27 wherein said volatile halide is hydrogen chloride.

* * * * *